(12) United States Patent
Xia et al.

(10) Patent No.: US 8,119,112 B2
(45) Date of Patent: Feb. 21, 2012

(54) OPHTHALMIC COMPOSITIONS WITH AN AMPHOTERIC SURFACTANT AND HYALURONIC ACID

(75) Inventors: Erning Xia, Penfield, NY (US); Susan E. Burke, Batavia, NY (US); Srini Venkatesh, Pittsford, NY (US); Vicki Barniak, Fairport, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 0 days.

(21) Appl. No.: 12/203,384

(22) Filed: Sep. 3, 2008

(65) Prior Publication Data
US 2009/0196846 A1  Aug. 6, 2009

Related U.S. Application Data

(63) Continuation of application No. 12/023,509, filed on Jan. 31, 2008.

(51) Int. Cl.
*A61K 31/74* (2006.01)
(52) U.S. Cl. .................................... 424/78.04; 514/912
(58) Field of Classification Search .............. 424/78.04; 514/912
See application file for complete search history.

(56) References Cited

U.S. PATENT DOCUMENTS

| | | | |
|---|---|---|---|
| 4,758,595 A | 7/1988 | Ogunbiyi et al. | |
| 5,358,706 A | 10/1994 | Marlin et al. | |
| 5,559,104 A | 9/1996 | Romeo et al. | |
| 5,765,579 A * | 6/1998 | Heiler et al. ................. | 134/42 |
| 5,770,628 A | 6/1998 | Cantoro | |
| 6,080,714 A | 6/2000 | Overkempe et al. | |
| 6,277,365 B1 | 8/2001 | Ellis et al. | |
| 6,528,465 B1 | 3/2003 | Cantoro | |
| 6,930,077 B2 | 8/2005 | Glick et al. | |
| 7,105,473 B2 | 9/2006 | Glick et al. | |
| 7,135,442 B2 | 11/2006 | Schwind et al. | |
| 2004/0063591 A1 | 4/2004 | Borazjani et al. | |
| 2004/0253280 A1 | 12/2004 | Chowhan et al. | |
| 2005/0074467 A1 | 4/2005 | Fujita et al. | |
| 2005/0152951 A1 | 7/2005 | Lloyd | |
| 2005/0196370 A1 | 9/2005 | Yu et al. | |
| 2005/0226841 A1 | 10/2005 | Yu et al. | |
| 2005/0260280 A1 | 11/2005 | Cook et al. | |
| 2005/0266089 A1 | 12/2005 | Cook et al. | |
| 2006/0100173 A1 | 5/2006 | Powell | |
| 2007/0059276 A1 | 3/2007 | Bergman et al. | |
| 2007/0286767 A1 | 12/2007 | Burke et al. | |
| 2008/0311070 A1 * | 12/2008 | Burke et al. ............... | 424/78.04 |

FOREIGN PATENT DOCUMENTS

| | | |
|---|---|---|
| EP | 0833609 B1 | 4/1998 |
| KR | 98-154371 | 7/1998 |
| WO | WO 01/57172 | 8/2001 |
| WO | WO 2008/049042 A | 4/2008 |
| WO | WO 2008/157140 A | 12/2008 |

OTHER PUBLICATIONS

Office Action, "U.S. Appl. No. 12/109,599," (Mar. 3, 2010).
EP Official Action, "EP App. 08167027.5-2123," (Jan. 19, 2010).
Berry et al., "Hyaluronan in dry eye and contact lens wearers," Lacrimal Gland, Tear Film, and Dry Eye Syndromes 2, Advances in Experimental Medicine and Biology, 1998, (vol. 438), (p. 785-790).
Fonn, "Targeting contact lens induced dryness and discomfort: what properties will make lenses more comfortable," Opt & Vision Sci, Apr. 2007, (vol. 84), (Issue. 4), (p. 279-285).
Frescura et al., "Evidence of hyaluronan in human tears and secretions of conjunctival cultures," Biochem Soc Transactions, 1994, (vol. 22), (p. 228S).
Fukuda et al., "Hyaluronic acid concentration in human tear fluids," Inv Oph & Visual Sci, (vol. 37), (Issue. 3), (p. S848), (Feb. 15, 1996).
Hamano et al., "Sodium hyaluronate eyedrops enhance tear film stability," Japan J Ophthal, 1996, (vol. 40), (p. 62-65).
Itoi et al., "Effect of sodium hyaluronate ophthalmic solution on peripheral staining of rigid contact lens wearers," CLAO Journal, Oct. 1995, (vol. 21), (Issue. 4), (p. 261-264).
Johnson et al., "Effectiveness of sodium hyaluronate eyedrops in the treatment of dry eye," Graefe's Arch Clin Exp Ophthalmol, 2006, (vol. 244), (p. 109-112).
Miyauchi et al., "A 26-week ophthalmic instillation test of sodium hyaluronate in rabbits," Pharmacometrics, 1993, (vol. 46), (Issue. 5), (p. 317-328).
Prabhasawat et al., "Performance profile of sodium hyalronate in patients with lipid tear deficiency: randomised, double-blind, controlled, exploratory study," Br J Ophthalmol, 2007, (vol. 91), (p. 47-50).
Pustorino et al., "Effect of bovine serum, hyaluronic acid and netilmicine on the in vitro adhesion of bacteria isolated from human-worn disposable soft contact lenses," Ann 1g, 1996, Inst of Microbiology, Italy, (vol. 8), (p. 469-475).
Prabhasawat et al., "Performance profile of sodium hyalronate in patients with lipid tear deficiency: randomised, double-blind, controlled, exploratory study," Br J Ophthalmol, 2007, (vol. 91), (p. 47-50).

(Continued)

*Primary Examiner* — Zohreh Fay
(74) *Attorney, Agent, or Firm* — Joseph Barrera

(57) ABSTRACT

Ophthalmic compositions that comprise 0.1 ppm to 10 ppm of a cationic antimicrobial component selected from the group consisting of biguanides, polymeric biguanides, quaternium ammonium compounds and any one mixture thereof; 0.005 wt. % to 0.15 wt. % of hyaluronic acid; and 0.01 wt. % to 1.0 wt. % of an amphoteric surfactant of general formula I

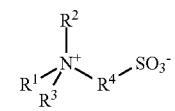

wherein $R^1$ is R or $-(CH_2)_n-NHC(O)R$, wherein R is a $C_8-C_{16}$alkyl optionally substituted with hydroxyl and n is 2, 3 or 4; $R^2$ and $R^3$ are each independently selected from methyl, ethyl, propyl or iso-propyl; and $R^4$ is a $C_2-C_8$alkylene optionally substituted with hydroxyl. The invention is also direct to the use of the ophthalmic compositions to clean and disinfect contact lenses, and in particular, soft, silicone hydrogel contact lenses.

12 Claims, 5 Drawing Sheets

OTHER PUBLICATIONS

Pustorino et al., "Effect of bovine serum, hyaluronic acid and netilmicine on the in vitro adhesion of bacteria isolated from human-worn disposable soft contact lenses," Ann 1g, 1996, Inst of Microbiology, Italy, (vol. 8), (p. 469-475).

Sand et al., "Sodium hyaluronate in the treatment of keratoconjunctivitis sicca. A double masked clinical trial," Acta Ophthalmol, 1989, p. 181-183.

Lapcik, L., et al., Hyaluronan: Preparation, Structure, Properties and Application, Chemical Reviews, Dec. 1998, vol. 98, No. 8, pp. 2663-2684.

Internet Publication, HyaCare (Novozymes) (Jan. 14, 2008).

Hirai, et al., Effects of Various Lubricants on Corneal Surface Regularity in Rabbits, J. Ocular Pharmacology and Therapeutics, Oct. 2005, vol. 1, Issue 5, pp. 376-381.

Debbasch, et al., Cytoprotective Effects of Hyaluronic Acid and Carbomer 934P in Ocular Surface Epithelial Cells, Investigative Ophthalmic & Visual Science, Nov. 2002, vol. 43, Issue 11, pp. 3409-3415.

Geyer, et al., A New Multipurpose Solution with Hyaluronate and Allantoin for All Types of Soft Contact Lenses, Lapis Lazuli Int., National Contact Lens Congress, Mar. 19-20, 2006.

Aqua Balance, "Product Description,", 2003.

510(K) Summary of Safety and Effectiveness, "Lapis Lazuli International NV for Eye See (tm) Multipurpose, Contact Lens Solution," (Jul. 24, 2007).

* cited by examiner

OPHTHALMIC COMPOSITIONS WITH AN AMPHOTERIC SURFACTANT AND HYALURONIC ACID

This continuation-in-part application claims benefit under 35 U.S.C. §120 to pending U.S. patent application Ser. No. 12/023,509 filed Jan. 31, 2008.

The present invention relates to ophthalmic compositions with an amphoteric surfactant and hyaluronic acid. The invention is also directed to the use of the ophthalmic compositions to clean and disinfect contact lenses.

BACKGROUND OF THE INVENTION

During normal use, contact lenses become soiled or contaminated with a wide variety of compounds that can degrade lens performance. For example, a contact lens will become soiled with biological materials such as proteins or lipids that are present in the tear fluid and which adhere to the lens surface. Also, by handling of the contact lens, sebum (skin oil) or cosmetics or other materials can soil the contact lens. These biological and external contaminants can affect visual acuity and patient comfort. Accordingly, it is important to remove any debris from the lens surface for continued comfortable use with a lens care solution that contains one or more cleaning components.

Ophthalmic compositions formulated as a lens care solution must also contain one or more disinfectant components. Presently, the two most popular disinfectant components are poly(hexamethylene biguanide), at times referred to as PHMB or PAPB, and polyquaternium-1.

As stated, PHMB is presently used in contact, lens care solutions. These PHMB-based care solutions represent a significant improvement in patient comfort and antimicrobial effectiveness compared to most other antimicrobial components. However, as with any antimicrobial component there remains a tradeoff between the concentration of the antimicrobial component in the solution and the comfort experienced by the patient. Due to its wide commercial acceptance, extensive efforts have been directed to improve the antimicrobial efficacy or the comfort level to the patient by chemically modifying PHMB.

An alternative approach to improving patient comfort has been the introduction of comfort agents or hydrating agents to the lens care solutions. For example, U.S. Pat. No. 7,135,442 describes the use of dexpanthenol in combination with the sugar alcohol, sorbitol. It is said that the dexpanthenol helps to stabilize or minimize the disruption of the aqueous lachrymal layer by surfactants present in the lens care solutions.

U.S. Pat. No. 5,770,628 by Cantoro describes an ophthalmic, artificial tear composition that contains from 0.05% to 2% by weight hyaluronic acid (sodium hyaluronate). The viscoelastic properties of hyaluronic acid, that is, hard elastic under static conditions though less viscous under small shear forces enables hyaluronic acid to basically function as a shock absorber for ocular cells and tissues. Shortly thereafter, Cantoro, recognized that if one were to add a poloxamer surfactant to the artificial tear, hyaluronic acid formulation the solution could be used as a rewet drop. The poloxamer surfactant is said to clean or remove denatured tear proteins and other containments from extended wear contact lenses while the lenses were being worn. See U.S. Pat. No. 6,528,465.

PCT Application (Publication No. WO 01/057172) describes a contact lens care solution that includes a polysaccharide with a molecular weight of 5000 daltons or greater as a non-enzymatic protein remover (0.005 to 10 wt. %), a nonionic surfactant (0.01 to 10 wt. %) and a polymeric preservative (0.00001 to 1 wt. %). An exemplary solution is provided as Example No. 5. This solution includes 0.02 wt. % sodium hyaluronate, 1.0 wt. % poloxamine (Tetronics® 1107), 0.125 wt. % $Na_2EDTA$ and 1 ppm of PHMB in a phosphate buffer.

The application of fluorescein to the cornea and the subsequent subjective and qualitative interpretation of the observed response is an accepted and important diagnostic tool to assess the physiological status of the cornea surface. Clinicians are cautioned, however, not to extrapolate from the clear clinical significance of high intensity, gross staining associated with corneal lesions and disease down to the meaning of superficial punctate corneal staining. Superficial punctate patterns of fluorescein dye fluorescence are to be viewed differently from nonsuperficial coalesced injury-related staining based on their common characteristics (superficial, transient and asymptomatic). For an extensive background and review on this subject, one is referred to Ward, K. W., "*Superficial Punctate Fluorescein Staining of the Ocular Surface*", Optometry and Vision Science 2008, 85(1) 1.

Beginning in the 1980's, with the growing market of contact lens use, the number of descriptive case studies of superficial punctate corneal staining has increased in the scientific literature. Although the precise mechanisms that control the depth and extent of the fluorescence signal associated with superficial punctate corneal staining remains unclear, the studies as a whole do provide scientific support that such staining does not reflect corneal injury or toxicity. In fact, both epidemiological and experimental evidence demonstrates a lack of correlation between superficial punctate corneal staining and the institution of corneal infections. Nevertheless, there have been a few reports that attempt to characterize the intensity of superficial punctate corneal staining at 2-hours with corneal toxicity, or imply that there exists a correlation between such staining and the institution of corneal infections. Again, these reports offer no scientific or clinical data to support such assertions.

To alleviate any such concerns that may exist in the lens care solution market, Applicants sought out and developed ophthalmic compositions that exhibit relatively low, superficial punctate corneal staining following placement of hydrogel contact lenses soaked with the compositions. In fact, head-to-head the ophthalmic compositions described herein meet or exceed the superficial punctate corneal staining profile of the leading lens care solutions presently on the market.

SUMMARY OF THE INVENTION

The invention is directed to ophthalmic compositions comprising 0.1 ppm to 10 ppm of a cationic antimicrobial component selected from the group consisting of biguanides, polymeric biguanides, quaternium ammonium compounds and any one mixture thereof; 0.005 wt. % to 0.15 wt. % of hyaluronic acid; and 0.01 wt. % to 1.0 wt. % of an amphoteric surfactant of general formula I

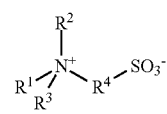

wherein $R^1$ is R or $-(CH_2)_n-NHC(O)R$, wherein R is a $C_8-C_{16}$ alkyl optionally substituted with hydroxyl and n is 2, 3 or 4; $R^2$ and $R^3$ are each independently selected from methyl, ethyl, propyl or iso-propyl; and $R^4$ is a $C_2-C_8$ alkylene optionally substituted with hydroxyl. The invention is also directed to the use of the ophthalmic compositions to clean and disinfect contact lenses, and in particular, soft, silicone, hydrogel contact lenses.

BRIEF DESCRIPTION OF THE DRAWINGS

The invention will be better understood from the following description and in consideration with the accompanying figures. It is to be expressly understood, however, that each of the figures is provided to further illustrate and describe the invention and is not intended to further limit the invention claimed.

DETAILED DESCRIPTION OF THE INVENTION

Figure 1:
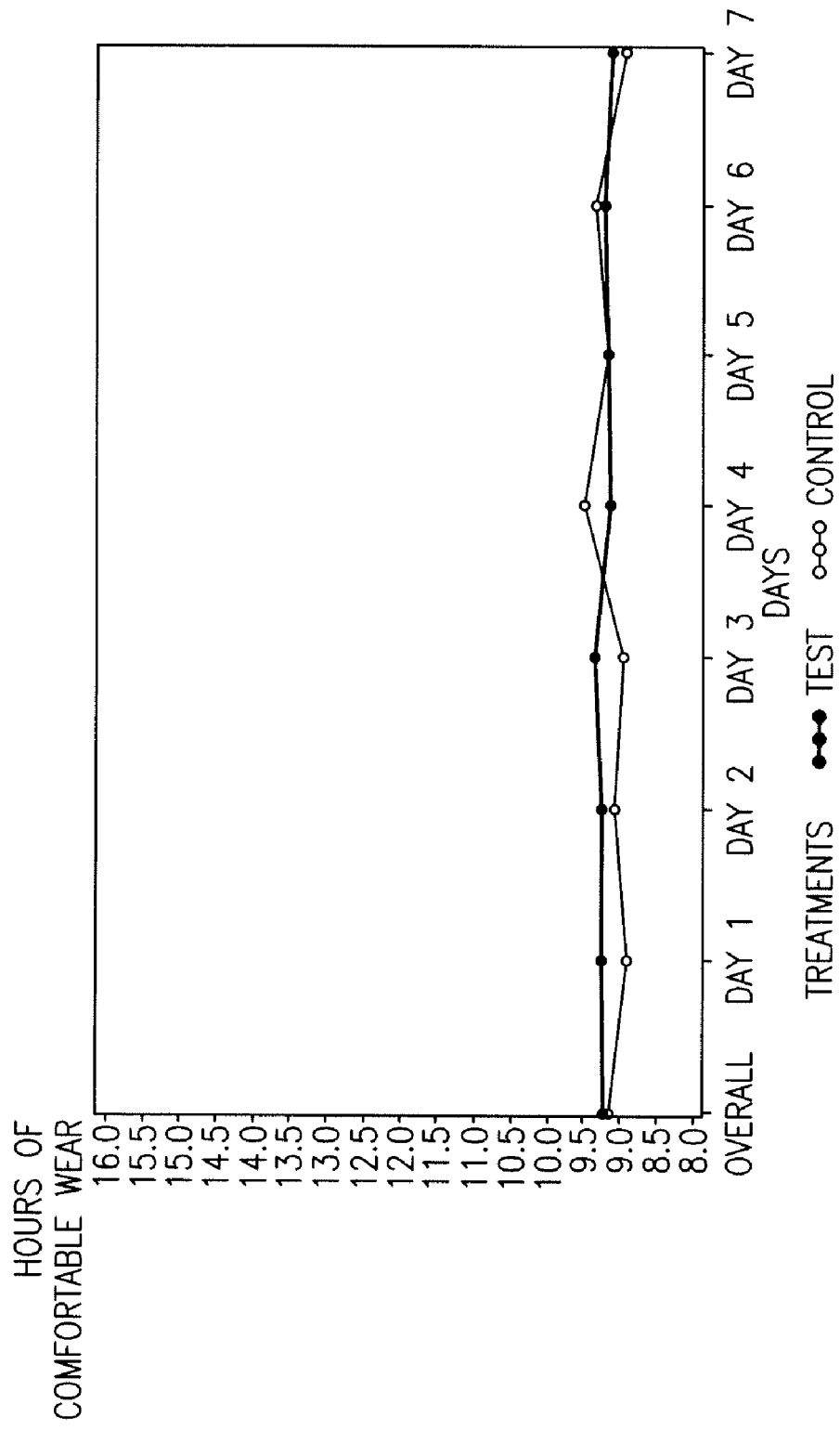
FIG. 1 is a plot showing the overall results of a clinical comparison between the test solution and control solution for hours of comfortable wear.

Applicants and others at Bausch & Lomb have developed and tested numerous ophthalmic formulations for use as lens care solutions. As mentioned above, such lens care solutions must satisfy a number of functional characteristics. First, the solutions must possess the cleaning ability to remove denatured tear proteins and tear lipids as well as other external contaminants. Second, the solutions must possess significant disinfecting ability against a number of different bacteria and fungal strains. Third, the solutions must remain comfortable to the contact lens patient with minimal stinging as well as provide a platform to provide additional comfort or protection to the ocular surface. Fourth, the solutions must not cause significant shrinkage or swelling of the many different contact lens materials, which in turn can lead to loss in visual acuity and unwanted or pronounced lens movement. Fifth, to address market perceptions, the solutions should have a superficial punctate corneal staining profile that equals or exceeds the staining profiles of present commercial lens care solutions.

In addition to all of the above characteristics, the solution must also pass a stringent test protocol that is referred by those in the art as "regimen" testing. An ophthalmic composition selectively formulated to clean and disinfect soft, silicone, hydrogel contact lenses must satisfy "regimen" testing for that formulation to obtain label approval from the Food and Drug Administration (FDA) as a no rub, contact lens cleaning and disinfecting solution. Many ophthalmic compositions during development fail to pass the regimen test with each and every silicone hydrogel contact lens in the U.S. market. A more detailed description of the regimen test is provided under the sub-heading Examples in this application. The ophthalmic compositions described and claimed address each of these functional requirements.

Applicant's developmental program and their investigations of numerous ophthalmic formulations led to at least three important insights. One, formulations that contain hyaluronic acid tend to exhibit less superficial punctate staining than those formulations that do not contain the anionic biopolymer. Two, the anionic sites of the hyaluronic acid appear to interact with the cationic-charged antimicrobial components, and in particular, hyaluronic acid interacts with both PHMB and polyquaternium-1. Three, the presence of the amphoteric surfactant of general formula I appears to counter the interaction between the anionic sites of hyaluronic and the cationic antimicrobial components. The result is a lens care solution that exhibits exceptional biocidal activity and biocidal stability with minimal or little impact on the observed benefits that hyaluronic acid provides.

The amphoteric surfactants of general formula I are surface-active compounds with both acidic and alkaline properties. The amphoteric surfactants of general formula I include a class of compounds known as betaines. The betaines are characterized by a fully quaternized nitrogen atom and do not exhibit anionic properties in alkaline solutions, which means that betaines are present only as zwitterions at near neutral pH.

All betaines are characterized by a fully quaternized nitrogen. In alkyl betaines, one of the alkyl groups of the quaternized nitrogen is an alkyl chain with eight to sixteen carbon atoms. One class of betaines is the sulfobetaines or hydroxysulfobetaines in which the carboxylic group of alkyl betaine is replaced by sulfonate. In hydroxysulfobetaines a hydroxy-group is positioned on one of the alkylene carbons that extend from the quaternized nitrogen to the sulfonate. In alkylamido betaines, an amide group is inserted as a link between the hydrophobic $C_8$-$C_{16}$ alkyl chain and the quaternized nitrogen.

Accordingly, the invention is directed to ophthalmic compositions comprising; 0.1 ppm to 10 ppm of a cationic antimicrobial component selected from the group consisting of biguanides, polymeric biguanides, quaternium ammonium compounds and any one mixture thereof; 0.005 wt. % to 0.15 wt. % of hyaluronic acid; and 0.01 wt. % to 1.0 wt. % of an amphoteric surfactant of general formula I

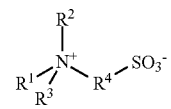

wherein $R^1$ is R or —$(CH_2)_n$—NHC(O)R, wherein R is a $C_8$-$C_{16}$ alkyl optionally substituted with hydroxyl and n is 2, 3 or 4; $R^2$ and $R^3$ are each independently selected from methyl, ethyl, propyl or iso-propyl; and $R^4$ is a $C_2$-$C_8$ alkylene optionally substituted with hydroxyl.

In one embodiment, the hyaluronic acid is present from 0.002 wt. % to 0.04 wt. %, and the cationic, antimicrobial component is poly(hexamethylene biguanide). Accordingly, one of the more preferred compositions comprises 0.5 ppm to 3.0 ppm of poly(hexamethylene biguanide); 0.002 wt. % to 0.04 wt. % hyaluronic acid; and 0.01 wt. % to 1 wt. % of an amphoteric surfactant of general formula I.

Certain sulfobetaines of general formula I are more preferred than others. For example, Zwitergent®3-10 available from Calbiochem Company, is a sulfobetaine of general formula I wherein $R^1$ is a straight, saturated alkyl with ten (10) carbons, $R^2$ and $R^3$ are each methyl and $R^4$ is —$CH_2CH_2CH_2$— (three carbons, (3)). Other sulfobetaines that can be used in the ophthalmic compositions include the corresponding Zwitergent®3-08 ($R^1$ is a is a straight, saturated alkyl with eight carbons), Zwitergent®93-12 ($R^1$ is a is a straight, saturated alkyl with twelve carbons), Zwitergent®3-14 ($R^1$ is a is a straight, saturated alkyl with fourteen carbons) and Zwitergent®3-16 ($R^1$ is a is a straight, saturated alkyl with sixteen carbons). Accordingly, some of the more preferred the ophthalmic composition will include a sulfobetaine of general formula II wherein $R^1$ is a $C_8$-$C_{16}$alkyl and $R^2$ and $R^3$ is methyl.

In another embodiment, the amphoteric surfactant of general formula I is a hydroxysulfobetaine of general formula II

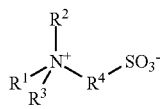

II wherein $R^1$ is a $C_8$-$C_{16}$alkyl substituted with at least one hydroxyl; $R^2$ and $R^3$ are each independently selected from methyl, ethyl, propyl or iso-propyl; and $R^4$ is a $C_2$-$C_8$alkylene substituted with at least one hydroxyl.

In another embodiment, the amphoteric surfactant is an alkylamido betaine of general formula III

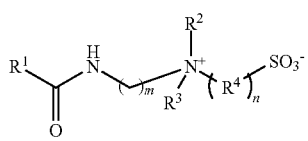

III wherein $R^1$ is a $C_8$-$C_{16}$alkyl, and m and n are independently selected from 2, 3, 4 or 5; $R^2$ and $R^3$ are each independently selected from a $C_1$-$C_4$alkyl optionally substituted with hydroxyl; and $R^4$ is a $C_2$-$C_8$alkylene optionally substituted with hydroxyl. The most common alkylamido betaines are alkylamidopropyl betaines, e.g., cocoamidopropyl dimethyl betaine and lauroyl amidopropyl dimethyl betaine.

Hyaluronic acid is a linear polysaccharide (long-chain biological polymer) formed by repeating disaccharide units consisting of D-glucuronic acid and N-acetyl-D-glucosamine linked by β(1-3) and β(1-4) glycosidic linkages. Hyaluronic acid is distinguished from the other glycosaminoglycans, as it is free from covalent links to protein and sulphonic groups. Hyaluronic acid is ubiquitous in animals, with the highest concentration found in soft connective tissue. It plays an important role for both mechanical and transport purposes in the body; e.g., it gives elasticity to the joints and rigidity to the vertebrate disks, and it is also an important component of the vitreous body of the eye.

Hyaluronic acid is accepted by the ophthalmic community as a compound that can protect biological tissues or cells from compressive forces. Accordingly, hyaluronic acid has been proposed as one component of a viscoelastic ophthalmic composition for cataract surgery. The viscoelastic properties of hyaluronic acid, that is, hard elastic under static conditions though less viscous under small shear forces enables hyaluronic acid to basically function as a shock absorber for cells and tissues. Hyaluronic acid also has a relatively large capacity to absorb and hold water. The stated properties of hyaluronic acid are dependent on the molecular weight, the solution concentration, and physiological pH. At low concentrations, the individual chains entangle and form a continuous network in solution, which gives the system interesting properties, such as pronounced viscoelasticity and pseudoplasticity that is unique for a water-soluble polymer at low concentration.

As stated, the compositions will also include an antimicrobial component selected from quarternary ammonium compounds (including small molecules) and polymers and low and high molecular weight biguanides. For example, biguanides include the free bases or salts of alexidine, chlorhexidine, hexamethylene biguanides and their polymers, and combinations thereof. The salts of alexidine and chlorhexidine can be either organic or inorganic and include gluconates, nitrates, acetates, phosphates, sulfates, halides and the like.

In a preferred embodiment, the composition will include a polymeric biguanide known as poly(hexamethylene biguanide) (PHMB or PAPB) commercially available from Zeneca, Wilmington, Del. under the trademark Cosmocil™ CQ. The PHMB is present in the compositions from 0.2 ppm to 5 ppm or from 0.5 ppm to 2 ppm.

Another biguanide of interest is 1,1'-hexamethylene-bis[5-(2-ethylhexyl)biguanide], which is referred to in the art as "alexidine". The alexidine is present in the compositions from 0.5 ppm to 5 ppm or from 0.5 ppm to 2 ppm.

One of the more common quaternary ammonium compounds is α-[4-tris(2-hydroxyethyl)-ammonium chloride-2-butenyl]poly[1-dimethyl ammonium chloride-2-butenyl]-ω-tris(2-hydroxyethyl) ammonium chloride, also referred to in the art as polyquaternium-1. Quaternary ammonium compounds are generally referred to in the art as "polyquaternium" disinfectants, and are identified by a particular number following the designation such as polyquaternium-1, polyquaternium-10 or polyquaternium-42. Polyquaternium-1 is present in the ophthalmic compositions from 0.5 ppm to 3 ppm. Attempts to increase the concentration of polyquaternium-1 beyond 3 ppm in the compositions results in the formation of a precipitate. The precipitate is believed to be the complexation product of hyaluronic acid and polyquaternium-1.

Polyquaternium-42 is also one of the more preferred polyquaternium disinfectants, see, U.S. Pat. No. 5,300,296. Polyquaternium-42 is present in the ophthalmic compositions from 5 ppm to 50 ppm.

It is to be understood by those in the art that the compositions can include one or more of the antimicrobial components described above. For example, in one embodiment, the ophthalmic compositions include polyquaternium-1 in combination with a biguanide antimicrobial component such as poly(hexamethylene biguanide). The polyquaternium-1 is present in relatively low concentrations, that is, from 0.5 ppm to 3 ppm, relative to the reported concentration of polyquaternium-1 in both Opti-Free®Express and Opti-Free®Replenish. Applicants believe that the polyquaternium-1 and the PHMB, in combination, may enhance the biocidal efficacy of the ophthalmic compositions.

Contact Lens Care Compositions

The contact lens care solutions will very likely include a buffer system. By the terms "buffer" or "buffer system" is meant a compound that, usually in combination with at least one other compound, provides a buffering system in solution that exhibits buffering capacity, that is, the capacity to neutralize, within limits, either acids or bases (alkali) with relatively little or no change in the original pH. Generally, the buffering components are present from 0.05% to 2.5% (w/v) or from 0.1% to 1.5% (w/v).

The term "buffering capacity" is defined to mean the millimoles (mM) of strong acid or base (or respectively, hydrogen or hydroxide ions) required to change the pH by one unit when added to one liter (a standard unit) of the buffer solution. The buffer capacity will depend on the type and concentration of the buffer components. The buffer capacity is measured from a starting pH of 6 to 8, preferably from 7.4 to 8.4.

Borate buffers include, for example, boric acid and its salts, for example, sodium borate or potassium borate. Borate buffers also include compounds such as potassium tetraborate or potassium metaborate that produce borate acid or its salt in solutions. Borate buffers are known for enhancing the efficacy of certain polymeric biguanides. For example, U.S. Pat. No. 4,758,595 to Ogunbiyi et al. describes that a contact-lens solution containing PHMB can exhibit enhanced efficacy if combined with a borate buffer.

A phosphate buffer system preferably includes one or more monobasic phosphates, dibasic phosphates and the like. Particularly useful phosphate buffers are those selected from phosphate salts of alkali and/or alkaline earth metals. Examples of suitable phosphate buffers include one or more of sodium dibasic phosphate ($Na_2HPO_4$), sodium monobasic phosphate ($NaH_2PO_4$) and potassium monobasic phosphate ($KH_2PO_4$). The phosphate buffer components frequently are used in amounts from 0.01% or to 0.5% (w/v), calculated as phosphate ion.

Other known buffer compounds can optionally be added to the lens care compositions, for example, citrates, citric acid, sodium bicarbonate, TRIS, and the like. Other ingredients in the solution, while having other functions, may also affect the buffer capacity, e.g., propylene glycol or glycerin.

A preferred buffer system is based upon boric acid/borate, a mono and/or dibasic phosphate salt/phosphoric acid or a combined boric/phosphate buffer system. For example a combined boric/phosphate buffer system can be formulated from a mixture of boric acid/sodium borate and a monobasic/dibasic phosphate. In a combined boric/phosphate buffer system, the phosphate buffer is used (in total) at a concentration of 0.004 to 0.2 M (Molar), preferably 0.04 to 0.1 M. The borate buffer (in total) is used at a concentration of 0.02 to 0.8 M, preferably 0.07 to 0.2 M.

The lens care solutions can also include an effective amount of a surfactant component, in addition to the amphoteric surfactant of general formula I, a viscosity inducing or thickening component, a chelating or sequestering component, or a tonicity component. The additional component or components can be selected from materials which are known to be useful in contact lens care solutions and are included in amounts effective to provide the desired functional characteristic.

Suitable surfactants can be cationic or nonionic, and are typically present (individually or in combination) in amounts up to 2% w/v. One preferred surfactant class are the nonionic surfactants. The surfactant should be soluble in the lens care solution and non-irritating to eye tissues. Many nonionic surfactants comprise one or more chains or polymeric components having oxyalkylene (—O—R—) repeats units wherein R has 2 to 6 carbon atoms. Preferred non-ionic surfactants comprise block polymers of two or more different kinds of oxyalkylene repeat units, which ratio of different repeat units determines the HLB of the surfactant. Satisfactory non-ionic surfactants include polyethylene glycol esters of fatty acids, e.g. coconut, polysorbate, polyoxyethylene or polyoxypropylene ethers of higher alkanes ($C_{12}$-$C_{18}$). Examples of this class include polysorbate 20 (available under the trademark Tween® 20), polyoxyethylene (23) lauryl ether (Brij® 35), polyoxyethyene (40) stearate (Myrj®52), polyoxyethylene (25) propylene glycol stearate (Atlas® G 2612). Still another preferred surfactant is tyloxapol.

A particular non-ionic surfactant consisting of a poly(oxypropylene)-poly(oxyethylene) adduct of ethylene diamine having a molecular weight from about 6,000 to about 24,000 daltons wherein at least 40 weight percent of said adduct is poly(oxyethylene) has been found to be particularly advantageous for use in cleaning and conditioning both soft and hard contact lenses. The CTFA Cosmetic Ingredient Dictionary's adopted name for this group of surfactants is poloxamine. Such surfactants are available from BASF Wyandotte Corp., Wyandotte, Mich., under Tetronic®. Particularly good results are obtained with poloxamine 1107 or poloxamine 1304. The foregoing poly(oxyethylene) poly(oxypropylene) block polymer surfactants will generally be present in a total amount from 0.0 to 2% w/v, from 0. to 1% w/v, or from 0.2 to 0.8% w/v An analogous of series of surfactants, for use in the lens care compositions, is the poloxamer series which is a poly (oxyethylene) poly(oxypropylene) block polymers available under Pluronic® (commercially available form BASF). In accordance with one embodiment of a lens care composition the poly(oxyethylene)-poly(oxypropylene) block copolymers will have molecular weights from 2500 to 13,000 daltons or from 6000 to about 12,000 daltons. Specific examples of surfactants which are satisfactory include: poloxamer 108, poloxamer 188, poloxamer 237, poloxamer 238, poloxamer 288 and poloxamer 407. Particularly good results are obtained with poloxamer 237 or poloxamer 407. The foregoing poly(oxyethylene) poly(oxypropylene) block polymer surfactants will generally be present in a total amount from 0.0 to 2% w/v, from 0. to 1% w/v, or from 0.2 to 0.8% w/v.

The lens care solutions can also include a phosphonic acid, or its physiologically compatible salt, that is represented by the following formula:

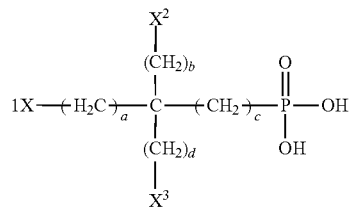

wherein each of a, b, c, and d are independently selected from integers from 0 to 4, preferably 0 or 1; $X^1$ is a phosphonic acid group (i.e., $P(OH)_2O$), hydroxy, amine or hydrogen; and $X^2$ and $X^3$ are independently selected from the group consisting of halogen, hydroxy, amine, carboxy, alkylcarbonyl, alkoxycarbonyl, or substituted or unsubstituted phenyl, and methyl. Exemplary substituents on the phenyl are halogen, hydroxy, amine, carboxy and/or alkyl groups. A particularly preferred species is that wherein a, b, c, and d in are zero, specifically the tetrasodium salt of 1-hydroxyethylidene-1,1-diphosphonic acid, also referred to as tetrasodium etidronate, commercially available from Monsanto Company as DeQuest® 2016 diphosphonic acid sodium salt or phosphonate.

The lens care solutions can include dexpanthenol, which is an alcohol of pantothenic acid, also called Provitamin B5, D-pantothenyl alcohol or D-panthenol. It has been stated that dexpanthenol may play a role in stabilizing the lachrymal film at the eye surface following placement of a contact lens on the eye. Dexpanthenol is preferably present in the solution in an amount from 0.2 to 5%/v, from 0.5 to 3% w/v, or from 1 to 2% w/v.

The contact lens care solutions can also include a sugar alcohol such as sorbitol or xylitol. Typically, dexpanthenol is used in combination with the sugar alcohol. The sugar alcohol is present in the lens care compositions in an amount from 0.4 to 5% w/v or from 0.8 to 3% w/v.

The lens care solutions can also include one or more neutral or basic amino acids. The neutral amino acids include: the alkyl-group-containing amino acids such as alanine, isoleucine, valine, leucine and proline; hydroxyl-group-containing amino acids such as serine, threonine and 4-hydroxyproline; thio-group-containing amino acids such as cysteine, methionine and asparagine. Examples of the basic amino acid include lysine, histidine and arginine. The one or more neutral or basic amino acids are present in the compositions at a total concentration of from 0.1 to 3% w/v.

The lens care solutions can also include glycolic acid, asparatic acid or any mixture of the two at a total concentration of from 0.001% to 4% (w/v) or from 0.01% to 2.0% (w/v). In addition, the combined use of one or more amino acids and glycolic acid and/or asparatic acid can lead to a reduction in the change of the size of the contact lens due to swelling and shrinkage following placement in the lens solution.

The lens care solutions can also include one or more comfort or cushioning components, in addition to the hyaluronic acid. The comfort component can enhance and/or prolong the cleaning and wetting activity of the surfactant component and/or condition the lens surface rendering it more hydrophilic (less lipophilic) and/or to act as a demulcent on the eye. The comfort component is believed to cushion the impact on the eye surface during placement of the lens and serves also to alleviate eye irritation.

Suitable comfort components include, but are not limited to, water soluble natural gums, cellulose-derived polymers and the like. Useful natural gums include guar gum, gum tragacanth and the like. Useful cellulose-derived comfort components include cellulose-derived polymers, such as hydroxypropyl cellulose, hydroxypropylmethyl cellulose, carboxymethyl cellulose, methyl cellulose, hydroxyethyl cellulose and the like. A very useful comfort component is hydroxypropylmethyl cellulose (HPMC). Some non-cellulose comfort components include propylene glycol or glycerin. The comfort components are typically present in the solution from 0.01% to 1% (w/v).

One preferred comfort agent that is believed to maintain a hydrated corneal surface is polyvinylpyrrolidone (PVP). PVP is a linear homopolymer or essentially a linear homopolymer comprising at least 90% repeat units derived from 1-vinyl-2-pyrrolidone monomer, the remainder of the monomer composition can include neutral monomer, e.g., vinyl or acrylates. Other synonyms for PVP include povidone, polyvidone, 1-vinyl-2-pyrrolidinone, and 1-ethenyl-2-pyrolionone (CAS registry number 9003-39-8). The PVP will preferably have a weight average molecular weight from 10,000 to 250,000 or from 30,000 to 100,000. Such materials are sold by various companies, including ISP Technologies, Inc. under the trademark PLASDONE®K-29/32, from BASF under the trademark KOLLIDON®, for example, KOLLIDON® K-30 or K-90. It is also preferred that one use pharmaceutical grade PVP.

The lens care solutions can also include one or more chelating components to assist in the removal of lipid and protein deposits from the lens surface following daily use. Typically, the ophthalmic compositions will include relatively low amounts, e.g., from 0.005% to 0.05% (w/v) of ethylenediaminetetraacetic acid (EDTA) or the corresponding metal salts thereof such as the disodium salt, $Na_2EDTA$.

One possible alternative to the chelator $Na_2EDTA$ or a possible combination with $Na_2EDTA$, is a disuccinate of formula IV below or a corresponding salt thereof;

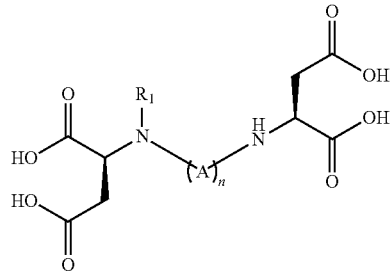

IV wherein $R_1$ is selected from hydrogen, alkyl or —C(O)alkyl, the alkyl having one to twelve carbons and optionally one or more oxygen atoms, A is a methylene group or an oxyalkylene group, and n is from 2 to 8. In one embodiment, the disuccinate is S,S-ethylenediamine disuccinate (S,S-EDDS) or a corresponding salt thereof. One commercial source of S,S-EDDS is represented by Octaquest® E30, which is commercially available from Octel. The chemical structure of the trisodium salt of S,S-EDDS is shown below. The salts can also include the alkaline earth metals such as calcium or magnesium. The zinc or silver salt of the disuccinate can also be used in the ophthalmic compositions.

Still another class of chelators include alkyl ethylenediaminetriacetates such as nonayl ethylenediaminetriacetate. See, U.S. Pat. No. 6,995,123 for a more complete description of such agents.

The lens care solutions will typically include an effective amount of a tonicity adjusting component. Among the suitable tonicity adjusting components that can be used are those conventionally used in contact lens care products such as various inorganic salts. Sodium chloride and/or potassium chloride and the like are very useful tonicity components. The amount of tonicity adjusting component is effective to provide the desired degree of tonicity to the solution.

The lens care solutions will typically have an osmolality in the range of at least about 200 mOsmol/kg for example, about 300 or about 350 to about 400 mOsmol/kg. The lens care solutions are substantially isotonic or hypertonic (for example, slightly hypertonic) and are ophthalmically acceptable.

One exemplary ophthalmic composition is formulated as a contact lens disinfecting solution prepared with the components and amounts of each listed in Table 1.

TABLE 1

| Component | Minimum Amount (wt. %) | Maximum Amount (wt. %) | Preferred Amount (wt. %) |
|---|---|---|---|
| boric acid | 0.10 | 1.0 | 0.64 |
| sodium borate | 0.01 | 0.20 | 0.1 |
| sodium chloride | 0.20 | 0.80 | 0.49 |
| Zwitergent ® 3-10 | 0.005 | 0.80 | 0.1 |
| hyaluronic acid | 0.005 | 0.05 | 0.01 |
| Tetronic ® 1107 | 0.05 | 2.0 | 1.00 |
| $Na_2EDTA$ | 0.005 | 0.15 | 0.03 |
| PHMB | 0.2 ppm | 2 ppm | 1.3 ppm |
| polyquaternium-1 | 0.5 ppm | 5 ppm | 1 ppm |

Another contact lens solution includes the following ingredients listed in Table 2.

TABLE 2

| Component | Minimum Amount (wt. %) | Maximum Amount (wt. %) | Preferred Amount (wt. %) |
|---|---|---|---|
| sorbitol or xylitol | 0.5 | 5 | 3 |
| poloxamer 407 | 0.05 | 1.0 | 0.10 |
| sodium phosphate, dihydrogen | 0.10 | 0.8 | 0.46 |
| dexpanthenol | 0.01 | 1.0 | 0.03 |
| zwitergent ® 3-10 | 0.01 | 0.2 | 0.05 |
| hyaluronic acid | 0.005 | 0.03 | 0.01 |
| Na$_2$EDTA | 0.005 | 0.3 | 0.1 |
| PHMB | 0.2 ppm | 2 ppm | 1 ppm |

Other contact lens solutions according includes the following ingredients listed in Tables 3 to 5.

TABLE 3

| Component | Minimum Amount (wt. %) | Maximum Amount (wt. %) | Preferred Amount (wt. %) |
|---|---|---|---|
| NaCl/KCl | 0.2 | 1.0 | 0.50 |
| propylene glycol | 0.1 | 1.0 | 0.50 |
| poloxamer 237 | 0.01 | 0.20 | 0.05 |
| phosphate monobasic | 0.05 | 0.40 | 0.10 |
| phosphate dibasic | 0.05 | 0.4 | 0.12 |
| zwitergent ® 3-10 | 0.01 | 0.3 | 0.1 |
| hyaluronic acid | 0.005 | 0.02 | 0.008 |
| Na$_2$EDTA | 0.005 | 0.3 | 0.1 |
| PHMB | 0.2 ppm | 2 ppm | 1.1 ppm |
| polyquaternium-1 | 0.5 ppm | 3 ppm | 1 ppm |

TABLE 4

| Component | Minimum Amount (wt. %) | Maximum Amount (wt. %) | Preferred Amount (wt. %) |
|---|---|---|---|
| NaCl/KCl | 0.01 | 0.5 | 0.10 |
| sorbitol | 0.2 | 2.0 | 0.5 |
| Propylene glycol | 0.2 | 2.0 | 0.6 |
| Poloxamine 1304 | 0.01 | 0.2 | 0.05 |
| Boric acid | 0.1 | 1.0 | 0.60 |
| Sodium borate | 0.01 | 0.2 | 0.10 |
| Hydroxypropyl guar | 0.01 | 0.5 | 0.05 |
| zwitergent ® 3-10 | 0.01 | 0.2 | 0.05 |
| hyaluronic acid | 0.005 | 0.03 | 0.01 |
| Na$_2$EDTA | 0.02 | 0.1 | 0.05 |
| PHMB | 0.2 ppm | 2 ppm | 0.3 ppm |
| polyquaternium-1 | 0.5 ppm | 3 ppm | 1.5 ppm |

TABLE 5

| Component | Minimum Amount (wt. %) | Maximum Amount (wt. %) | Preferred Amount (wt. %) |
|---|---|---|---|
| NaCl/KCl | 0.05 | 0.5 | 0.10 |
| phosphate monobasic | 0.05 | 0.40 | 0.12 |
| phosphate dibasic | 0.05 | 0.4 | 0.21 |
| sorbitol | 0.5 | 2.0 | 1.0 |
| Poloxamine 904 | 0.02 | 0.5 | 0.10 |
| Povidone K90 | 0.05 | 0.5 | 0.10 |
| zwitergent ® 3-10 | 0.01 | 0.2 | 0.05 |
| hyaluronic acid | 0.005 | 0.03 | 0.01 |
| Na$_2$EDTA | 0.005 | 0.3 | 0.1 |
| PHMB | 0.2 ppm | 2 ppm | 1 ppm |
| polyquaternium-1 | 0.5 ppm | 3 ppm | 1.5 ppm |

As described, the ophthalmic compositions can be used to clean and disinfect contact lenses. In general, the contact lens solutions can be used as a daily or every other day care regimen known in the art as a "no-rub" regimen. This procedure includes removing the contact lens from the eye, rinsing both sides of the lens with a few milliliters of solution and placing the lens in a lens storage case. The lens is then immersed in fresh solution for at least two hours. The lens is the removed form the case, optionally rinsed with more solution, and repositioned on the eye.

Alternatively, a rub protocol would include each of the above steps plus the step of adding a few drops of the solution to each side of the lens, followed by gently rubbing the surface between ones fingers for approximately 3 to 10 seconds. The lens can then be, optionally rinsed, and subsequently immersed in the solution for at least two hours. The lenses are removed from the lens storage case and repositioned on the eye.

The ophthalmic compositions can be used with many different types of contact lenses including: (1) hard lenses formed from materials prepared by polymerization of acrylic esters, such as poly(methyl methacrylate) (PMMA), (2) rigid gas permeable (RGP) lenses formed from silicone acrylates and fluorosilicone methacrylates, (3) soft, hydrogel lenses, and (4) non-hydrogel elastomer lenses.

As an example, soft hydrogel contact lenses are made of a hydrogel polymeric material, a hydrogel being defined as a crosslinked polymeric system containing water in an equilibrium state. In general, hydrogels exhibit excellent biocompatibility properties, i.e., the property of being biologically or biochemically compatible by not producing a toxic, injurious or immunological response in a living tissue. Representative conventional hydrogel contact lens materials are made by polymerizing a monomer mixture comprising at least one hydrophilic monomer, such as (meth)acrylic acid, 2-hydroxyethyl methacrylate (HEMA), glyceryl methacrylate, N,N-dimethacrylamide, and N-vinylpyrrolidone (NVP). In the case of silicone hydrogels, the monomer mixture from which the copolymer is prepared further includes a silicone-containing monomer, in addition to the hydrophilic monomer. Generally, the monomer mixture will also include a crosslink monomer such as ethylene glycol dimethacrylate, tetraethylene glycol dimethacrylate, and methacryloxyethyl vinylcarbonate. Alternatively, either the silicone-containing monomer or the hydrophilic monomer may function as a crosslink agent.

The ophthalmic compositions can also be formulated as a contact lens rewetting eye drop solution. By way of example, the rewetting drops may be formulated according to any one of the foregoing formulations of Tables 1 to 5 above. Alternatively, the formulations may be modified by increasing the amount of surfactant; by reducing the amount of antimicrobial agent to a preservative amount and/or by adding a humectant and/or demulcent.

The ophthalmic compositions can be used as a preservative in formulations for treating patients with dry eye. In such a method, the ophthalmic composition is administered to the patient's eye, eye lid or to the skin surrounding the patient's eye. The compositions can be administered to the eyes irrespective of whether contact lenses are present in the eyes of the patient. For example, many people suffer from temporary or chronic eye conditions in which the eye's tear system fails to provide adequate tear volume or tear film stability necessary to remove irritating environmental contaminants such as dust, pollen, or the like.

The ophthalmic compositions can also be used as a preservative in pharmaceutical compositions such as nasal sprays, ear and eye drops, suppositories, and prescription and over-the-counter formulations containing a pharmaceutical active that are used or administered over time such as a cream, ointment, gel or solution.

In many instances, the ophthalmic compositions will include one or more active pharmaceutical agents. Generally, the active pharmaceutical agent is in one or more classes of ocular pharmaceuticals including, but not limited to anti-inflammatory agents, antibiotics, immunosuppressive agents, antiviral agents, antifungal agents, anesthetics and pain killers, anticancer agents, anti-glaucoma agents, peptide and proteins, anti-allergy agents.

EXAMPLES

Examples 1.-5 and Comparative Examples 1 and 2

Contact lens compositions of Example 1.-5. and Comparative Examples 1 and 2 listed in Table 6 are prepared using the following process (components are listed in wt. % unless noted in ppm). A volume of purified water equivalent to 85-90% of the total batch weight is added to a stainless steel mixing vessel. The following batch quantities of components are added to the water with stirring in the order listed: sodium chloride, edetate disodium, boric acid, sodium borate and poloxamine 1107. The solution is mixed (stirred) for not less than 10 minutes to ensure complete dissolution of each of the components. The solution is warmed to a temperature not less than 70° C. and the sodium hyaluronate is added. The warmed solution is stirred for at least 20 minutes until the sodium hyaluronate appears to be completely dissolved. The pH of the resulting solution is measured at room temperature, and if necessary, the pH is adjusted with 1N NaOH or 1N HCl (target pH=7.5). The solution is then heat sterilized at 121° C. for at least 30 minutes.

In a second stainless steel vessel, a measured amount of Zwittergent 3-10 required for the batch is added to a given amount of purified water, and the solution stirred for at least 30 minutes. The Zwittergent solution is aseptically transferred to the bulk solution through a sterilizing filter, and again the solution is stirred for at least 10 minutes.

In a third stainless steel vessel, a measured amount of PAPB required for the batch is added to a given amount of purified water, and the solution is stirred for at least 10 minutes. The PAPB solution is aseptically transferred to the bulk solution through a sterilizing filter, and again the solution is stirred for at least 10 minutes.

In a fourth stainless steel vessel, a measured amount of polyquaternium-1 required for the batch is added to a given amount of purified water, and the solution is stirred for at least 10 minutes. The polyquaternium-1 solution is aseptically transferred to the bulk solution through a sterilizing filter, and again the solution is stirred for at least 10 minutes. Purified water is then added to the bulk solution to bring to the batch weight. The final solution is stirred for at least 15 minutes.

TABLE 6

| | \multicolumn{7}{c}{Example} | | | | | | |
|---|---|---|---|---|---|---|---|
| | 1 | 2 | 3 | 4 | 5 | Comp. Ex. 1 | Comp. Ex. 2 |
| boric acid | 0.60 | 0.55 | 0.55 | 0.64 | 0.64 | 0.64 | 0.64 |
| sodium borate | 0.105 | 0.11 | 0.08 | 0.12 | 0.105 | 0.11 | 0.12 |
| sodium chloride | 0.50 | 0.45 | 0.45 | 0.50 | 0.50 | 0.50 | 0.50 |
| Na$_2$EDTA | 0.11 | 0.11 | 0.08 | 0.06 | 0.025 | 0.11 | 0.11 |
| Dequest ® 2016 | 0.05 | 0.1 | — | — | — | 0.1 | 0.1 |
| Tetronics ® 1107 | 1.0 | 1.0 | 1.0 | 1.0 | 1.0 | 1.0 | 1.0 |

TABLE 6-continued

| | Example | | | | | | |
|---|---|---|---|---|---|---|---|
| | 1 | 2 | 3 | 4 | 5 | Comp. Ex. 1 | Comp. Ex. 2 |
| sodium hyaluronate | 0.015 | 0.008 | 0.01 | 0.015 | 0.01 | 0.02 | 0.01 |
| Zwittergent ® 3-10 | 0.05 | 0.05 | 0.05 | 0.05 | 0.05 | — | — |
| PAPB (ppm) | 1.0 | 1.1 | 1.1 | 1.3 | 1.3 | 1.3 | 1.5 |
| polyquaternium-1 (ppm) | 1.0 | 1.0 | 1.0 | 1.0 | 1.0 | — | 1.0 |

Biocidal Stand-Alone Stability

In order to assess the activity of the formulation, samples are bottled in 4 oz PET containers and stored at ambient temperature, as well as elevated temperatures for a given period. The stand-alone biocidal efficacy of the samples is tested at designated intervals to determine the stability of the formulation with time for is disinfection activity. The "Stand-Alone Procedure for Disinfecting Products" is based on the Disinfection Efficacy Testing for Products dated May 1, 1997, prepared by the U.S. Food and Drug Administration, Division of Ophthalmic Devices. This performance requirement does not contain a rub procedure.

The stand-alone test challenges a disinfecting product with a standard inoculum of a representative range of microorganisms and establishes the extent of viability loss at predetermined time intervals comparable with those during which the product may be used. The primary criteria for a given disinfection period (corresponding to a potential minimum recommended disinfection period) is that the number of bacteria recovered per mL must be reduced by a mean value of not less than 3.0 logs within the given disinfection period. The number of mold and yeast recovered per ml must be reduced by a mean value of not less than 1.0 log within the minimum recommended disinfection time with no increase at four times the minimum recommended disinfection time.

The antimicrobial efficacy of each of the various compositions for the chemical disinfection and cleaning of contact lenses are evaluated in the presence of 10% organic soil using the stand-alone procedure. Microbial challenge inoculums are prepared using *Staphylococcus aureus* (ATCC 6538), *Pseudomonas aeruginosa* (ATCC 9027), *Serratia marcescens* (ATCC 13880), *Candida albicans* (ATCC 10231) and *Fusarium solani* (ATCC 36031). The test organisms are cultured on appropriate agar and the cultures are harvested using sterile Dulbecco's Phosphate Buffered Saline plus 0.05 percent weight/volume polysorbate 80 (DPBST) or a suitable diluent and transferred to a suitable vessel. Spore suspensions are filtered through sterile glass wool to remove hyphal fragments. *Serratia marcescens*, as appropriate, is filtered through a 1.2 µm filter to clarify the suspension.

After harvesting, the suspension is centrifuged at no more than 5000×g for a maximum of 30 minutes at a temperature of 20° C. to 25° C. The supernatant is decanted and resuspended in DPBST or other suitable diluent. The suspension is centrifuged a second time, and resuspended in DPBST or other suitable diluent. All challenge bacterial and fungal cell suspensions are adjusted with DPBST or other suitable diluent to $1\times10^7$ to $1\times10^8$ cfu/mL. The appropriate cell concentration may be estimated by measuring the turbidity of the suspension, for example, using a spectrophotometer at a preselected wavelength, for example, 490 nm. One tube is prepared containing a minimum of 10 mL of test solution per challenge organism. Each tube of the solution to be tested is inoculated with a suspension of the test organism sufficient to provide a final count of $1\times10^5$ to $1\times10^6$ cfu/mL, the volume of the inoculum not exceeding 1 percent of the sample volume.

Dispersion of the inoculum is ensured by vortexing the sample for at least 15 seconds. The inoculated product is stored at 10° C. to 25° C. Aliquots in the amount of 1.0 mL are taken of the inoculated product for determination of viable counts after certain time periods of disinfection.

The suspension is mixed well by vortexing vigorously for at least 5 sec. The 1.0 mL aliquots removed at the specified time intervals are subjected to a suitable series of decimal dilutions in validated neutralizing media. The suspensions are mixed vigorously and incubated for a suitable period of time to allow for neutralization of the microbial agent. The viable count of organisms is determined in appropriate dilutions by preparation of triplicate plates of trypticase soy agar (TSA) for bacteria and Sabouraud dextrose agar (SDA) for mold and yeast. The bacterial recovery plates are incubated at 30° C. to 35° C. for two to four days. The yeast recovery plates are incubated at 20° C. to 30° C. for two to four days. The mold recovery plates are incubated at 20° C. to 25° C. for three to seven days. The average number of colony forming units is determined on countable plates. Countable plates refer to 30 to 300 cfu/plates for bacteria and yeast, and 8 to 80 cfu/plate for mold except when colonies are observed only for the $10^0$ or $10^{-1}$ dilution plates. The microbial reduction is then calculated at the specified time points.

In order to demonstrate the suitability of the medium used for growth of the test organisms and to provide an estimation of the initial inoculum concentration, inoculum controls are prepared by dispersing an identical aliquot of the inoculum into a suitable diluent, for example, DPBST, using the same volume of diluent used to suspend the organism as listed above. Following inoculation in a validated neutralizing broth and incubation for an appropriate period of time, the inoculum control must be between $1.0 \times 10^5$ and $1.0 \times 10^6$ cfu/mL.

Biocidal stand-alone stability data was obtained with Example 5.

TABLE 7

Four-hour biocidal stand-alone stability in PET bottle at elevated temperatures for Example 5.

| Time point | Temp ° C. | Sa | Pa | Sm | Ca | Fs |
|---|---|---|---|---|---|---|
| $t_0$ | 25 | 4.7 | >4.7 | 3.8 | 3.3 | >4.3 |
| one month | 25 | 4.5 | >4.7 | 3.5 | 2.9 | 3.4 |
|  | 40 | >4.7 | >4.7 | 3.0 | 2.8 | 3.2 |
|  | 50 | 4.3 | 4.4 | 3.2 | 3.4 | 3.2 |
| two month | 25 | >4.8 | >4.5 | 4.2 | 2.1 | 1.7 |
|  | 30 | 4.8 | 4.5 | 3.7 | 2.5 | 3.3 |
|  | 40 | >4.8 | >4.5 | 3.9 | 2.9 | 1.9 |
|  | 50 | >4.8 | 4.3 | 3.9 | 2.5 | 3.1 |
| three month | 25 | >4.9 | 4.8 | 4.4 | 2.9 | 4.1 |
|  | 30 | 4.9 | >4.8 | 4.5 | 2.8 | 3.7 |
|  | 40 | >4.9 | >4.8 | 3.9 | 2.7 | 3.7 |
|  | 50 | >4.9 | >4.8 | 4.5 | 2.8 | 3.3 |
| six month | 40 | >4.7 | >4.6 | >4.7 | 3.1 | 3.1 |
| nine month | 40 | >4.8 | >4.7 | >4.6 | 2.5 | 2.9 |
| $t_0$ | Opti-Free ® Replenish 25° C. | 3.9 | >4.7 | 2.8 | 2.0 | 1.9 |

TABLE 8

Four-hour biocidal stand-alone stability in PET bottle at elevated temperatures for Comp. Ex. 1.

| Time point | Temp ° C. | Sa | Pa | Sm | Ca | Fs |
|---|---|---|---|---|---|---|
| $t_0$ | 25 | >4.6 | >4.6 | >4.7 | 2.1 | 3.0 |
| one month | 40 | 3.9 | >4.6 | >4.9 | 1.7 | 2.7 |
| two months | 40 | 3.0 | >4.7 | >4.6 | 2.0 | 3.2 |

TABLE 8-continued

Four-hour biocidal stand-alone stability in PET bottle at elevated temperatures for Comp. Ex. 1.

| Time point | Temp ° C. | Sa | Pa | Sm | Ca | Fs |
|---|---|---|---|---|---|---|
| three months | 25 | 2.7 | >4.7 | >4.7 | 1.6 | 1.9 |
|  | 40 | 2.7 | >4.7 | >4.7 | 1.4 | 1.8 |
| five months | 40 | 3.2 | NT | NT | 1.4 | 1.4 |
| six months | 25 | 2.8 | >4.6 | >4.6 | 2.4 | 3.0 |
|  | 40 | 2.4 | >4.6 | 4.5 | 1.6 | 1.2 |

NT—not tested

Regimen Testing with PureVision® Lenses

Regimen efficacy testing involves first incoluating both sides of the contact lenses with 0.01 mL of a suspension of $1.0 \times 10^7$-$1.0 \times 10^8$ CFU/mL of the test organism in organic soil solution. The inoculum is allowed to adsorb to each lens for 5-10 minutes at 20-25° C. After the absorption period, each side of the lenses are rinsed for 5 seconds with the test solution and then allowed to soak in the test solution stored in standard B&L lens cases for 4 hours. To recover the surviving challenged organisms, a given volume of validated neutralizing medium is placed in a filtration apparatus. The entire contents of a given lens case (lens and test solution) is transferred to the neutralizing medium in the filtration apparatus. After an appropriate neutralization exposure time, a vacuum is applied to the filtration apparatus to filter the solution. The lens is aseptically transferred to a bed of agar medium appropriate for the recovery of the test organism. A given amount of the same agar (at 40-50° C.) used in the bed is poured over the lens to cast it. The test filter is placed on the surface of agar medium appropriate to recover the test organism. Bacteria recovery plates are incubated for 2-4 days at 30-35° C., while yeast recovery plates are incubated for 3-5 days at 20-25° C. or 30-35° C. and mold recovery plates are incubated for 3-7 days at 20-25° C. Appropriate inoculum, lens inoculum, as well as, neutralizing and recovery controls are run for each experiment.

TABLE 8

No-rub Regimen data of Example 5 (test no. 1).

| | Avg. CFU | | | | |
|---|---|---|---|---|---|
| Lens | Sa | Pa | Sm | Ca | Fs |
| AcuVue ® 2 | 0 | 0.3 | 1.0 | 1.5 | 0.3 |
| AcuVue ® Advance | 0.3 | 0 | 0.5 | 0 | 0.3 |
| PureVision ® (HPMC) | 2.8 | 0 | 3.5 | 7.0 | 0 |
| O$_2$Optix ® | 0.3 | 0.3 | 0 | 3.3 | 0 |

TABLE 9

No-rub Regimen data of Example 5 (test no. 2).

| | Avg. CFU | | | |
|---|---|---|---|---|
| Lens | Sa | Pa | Ca | Fs |
| AcuVue ® 2 | 0 | 0.5 | 0 | 0 |
| AcuVue ® Advance | 0 | 2 | 0 | 0 |
| Soflens 38 ® | 0.8 | 1.0 | 0 | 0 |
| PureVision ® (HPMC) | 0 | 0 | 5 | 0 |
| O$_2$Optix ® | 0 | 0 | 0.3 | 0 |
| Night&Day ® | 0 | 1 | 0 | 0 |

TABLE 10

No-rub Regimen data of OptiFree ® Replenish.

| Lens | Avg. CFU Ca |
|---|---|
| Soflens 38 ® | 0 |
| AcuVue ® 2 | 0 |
| AcuVue ® Advance | 0 |
| O₂Optix ® | 53 |
| PureVision ® (HPMC | 55 |
| Night&Day ® | 75 |

TABLE 11

No-rub Regimen data with PureVision lenses for Comp. Ex. 1

| Lens | Avg. CFU Ca |
|---|---|
| PureVision ® (HPMC) | 13.7 |

Superficial Punctuate Corneal Staining at Two Hours

Each well of the lens cases was pre-treated (a single, 4-hour minimum soak) with either test solution or control solution. For each case, the well treated with test solution was randomly determined and the fellow well received the control solution. All PureVision® lenses were pre-treated (4-hour minimum soak), with either the test solution or control solution, in the pre-treated lens cases, following the same randomization used for the lens case wells. Prior to lens insertion, superficial punctate corneal staining was assessed with the slit lamp. After approximately 2 hours of lens wear, each subject returned. Lenses were removed, superficial punctate corneal staining profiles were reassessed with the slit lamp. The control solution is Opti-Free® Replenish.

TABLE 12

| Test Solution | No. of patients | normalized corneal staining extent (2 hr) | normalized corneal staining extent - control (2 hr) |
|---|---|---|---|
| Comp Ex. 1 | 23 | 0.91 ± 0.85 | 0.91 ± 1.31 |
| Comp Ex. 2 | 23 | 2.13 ± 1.14 | 0.39 ± 0.66 |
| Ex. 5 | 23 | 1.43 ± 1.16 | 0.70 ± 0.88 |

Lens Compatibility Testing

TABLE 13

30 Cycle lens compatibility data of commercial lenses with Example 5.

| Soft Contact Lens Type | Parameter | ISO Spec | 30 Cycles | Reverse 30 Cycles |
|---|---|---|---|---|
| ACUVUE ® 2 | Diameter | ±0.20 mm | In spec | In spec |
| | Estimated Base Curve | ±0.20 mm | In spec | In spec |
| ACUVUE ® | Diameter | ±0.20 mm | In spec | In spec |
| | Estimated Base Curve | ±0.20 mm | In spec | In spec |
| SofLens ® 66 Toric | Diameter | ±0.20 mm | In spec | In spec |
| | Estimated Base Curve | ±0.20 mm | In spec | In spec |
| SofLens ® 38 | Diameter | ±0.20 mm | In spec | In spec |
| | Estimated Base Curve | ±0.20 mm | In spec | In spec |
| ACUVUE ® ADVANCE | Diameter | ±0.20 mm | In spec | In spec |
| | Estimated Base Curve | ±0.20 mm | In spec | In spec |
| ACUVUE ® OASYS | Diameter | ±0.20 mm | In spec | In spec |
| | Estimated Base Curve | ±0.20 mm | In spec | In spec |
| NIGHT & DAY ® | Diameter | ±0.20 mm | In spec | In spec |
| | Estimated Base Curve | ±0.20 mm | In spec | In spec |
| O₂OPTIX ™ | Diameter | ±0.20 mm | In spec | In spec |
| | Estimated Base Curve | ±0.20 mm | In spec | In spec |
| PureVision ® | Diameter | ±0.20 mm | In spec | In spec |
| | Estimated Base Curve | ±0.20 mm | In spec | In spec |
| Biofinity ® | Diameter | ±0.20 mm | In spec | In spec |
| | Estimated Base Curve | ±0.20 mm | In spec | In spec |

Clinical Evaluation of Example 5 vs. Opti-Free® Replenish

A multi-center, masked, active-controlled, bilateral, parallel-group, two-week study was conducted with half of the subjects randomized to receive the lens care solution of Example 5 (test solution) and half to receive Opti-Free®Replenish (control solution) lens care solution. All subjects were dispensed a new pair of their habitual lenses (⅓ PureVision®, ⅓ Acuvue®Oasys, and ⅓ Night&Day® or O₂Optix®) and either the test or control lens care solution at the beginning of the study. The subjects were instructed to the use of the solutions and care of their lenses. Subjects were also required to complete a daily diary for the first week of the study and mail the completed study to their respective sponsor. The study included 361 subjects (347 completed study) of Asian descent with the demographics reported in Table 14.

TABLE 14

Clinical Demographics

| demographic | test | control |
|---|---|---|
| age, n | 175 | 175 |
| mean (sd) | 28.3 (7.4) | 27.4 (7.3) |
| min. max | 18, 54 | 18, 48 |
| gender n (%) | | |
| female | 125 (71.4) | 124 (69.1) |
| male | 50 (28.6) | 54 (30.9) |

TABLE 14-continued

| Clinical Demographics | | |
|---|---|---|
| demographic | test | control |
| daily wear time | | |
| mean (sd) | 11.9 (2.7) | 11.6 (2.6) |
| min. max | 6, 24 | 5, 24 |
| refraction sphere | | |
| (diopters), mean | −3.79 (1.86) | −3.96 (2.05) |
| min, max | −10.75, −0.50 | −10.25, 0.75 |
| refraction cylinder | | |
| (diopters), mean | −0.353 (0.36) | −0.40, (0.4) |
| min, max | −1.5, 0.0 | −1.75, 0.0 |

Study Results

Figure 2:
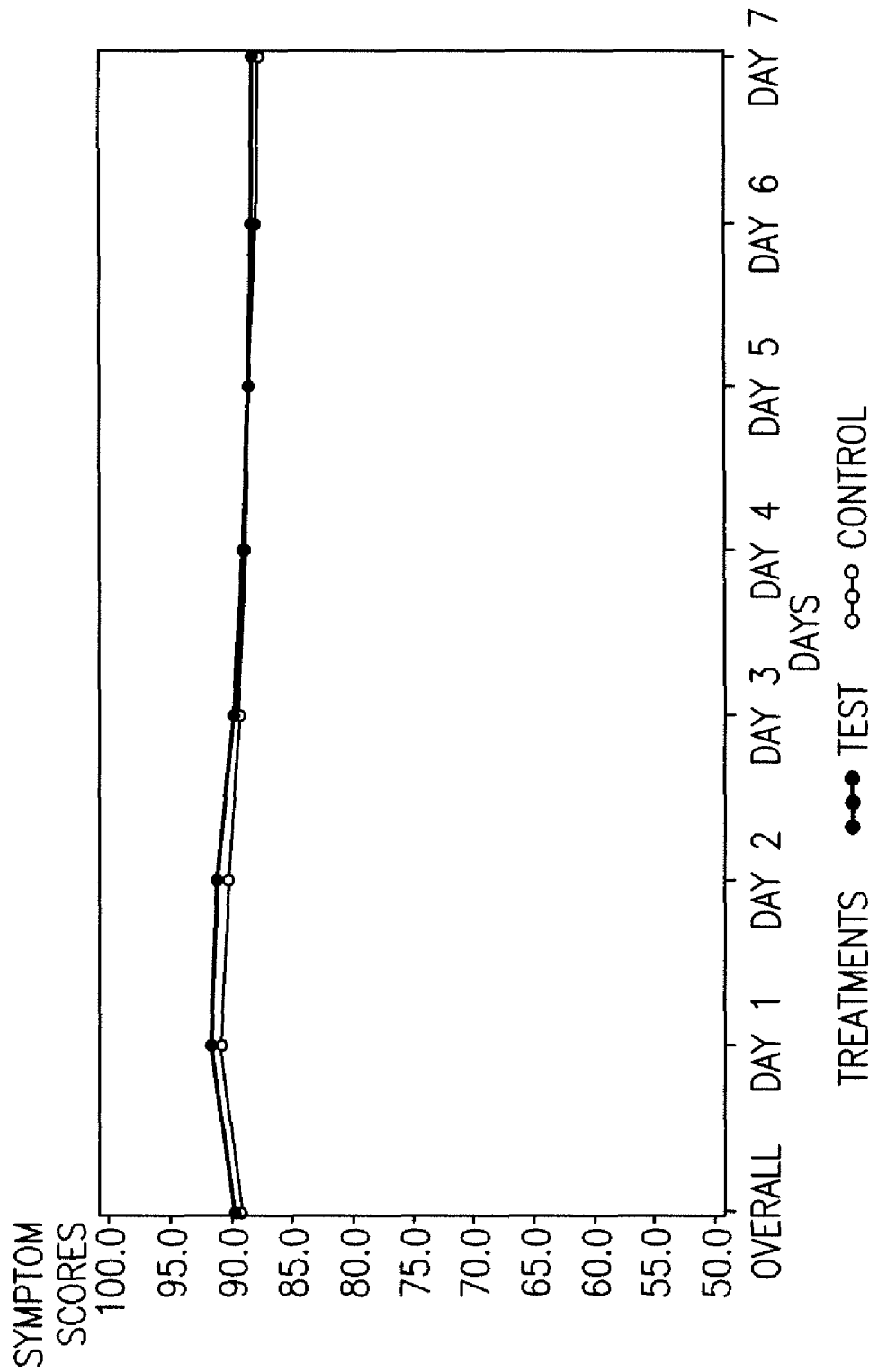
FIG. 2 is a plot showing the overall results of a clinical comparison between the test solution and control solution for cleanliness of lens at insertion.
Figure 3:
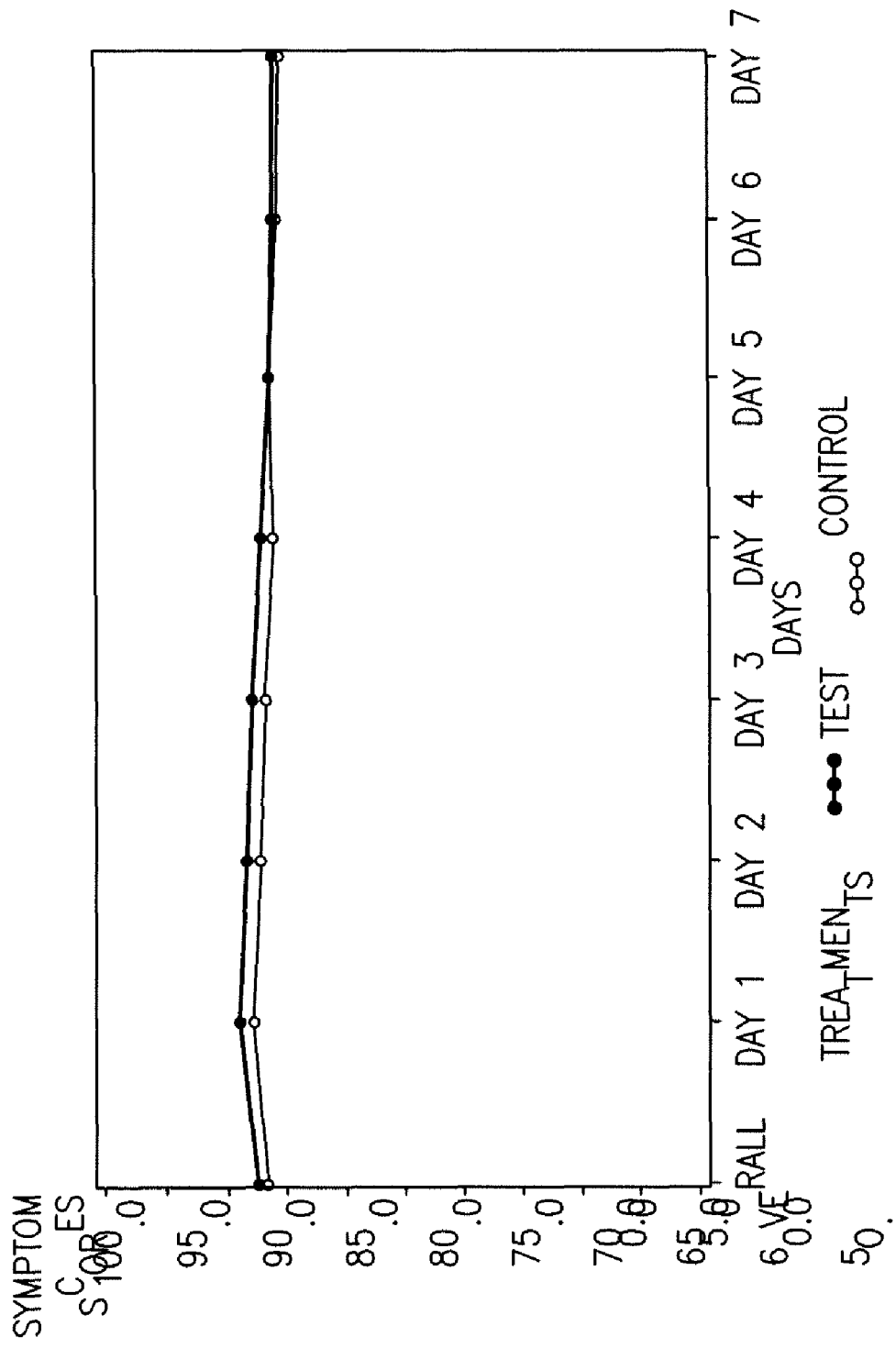
FIG. 3 is a plot showing the overall results of a clinical comparison between the test solution and control solution for comfort upon insertion.
Figure 4:
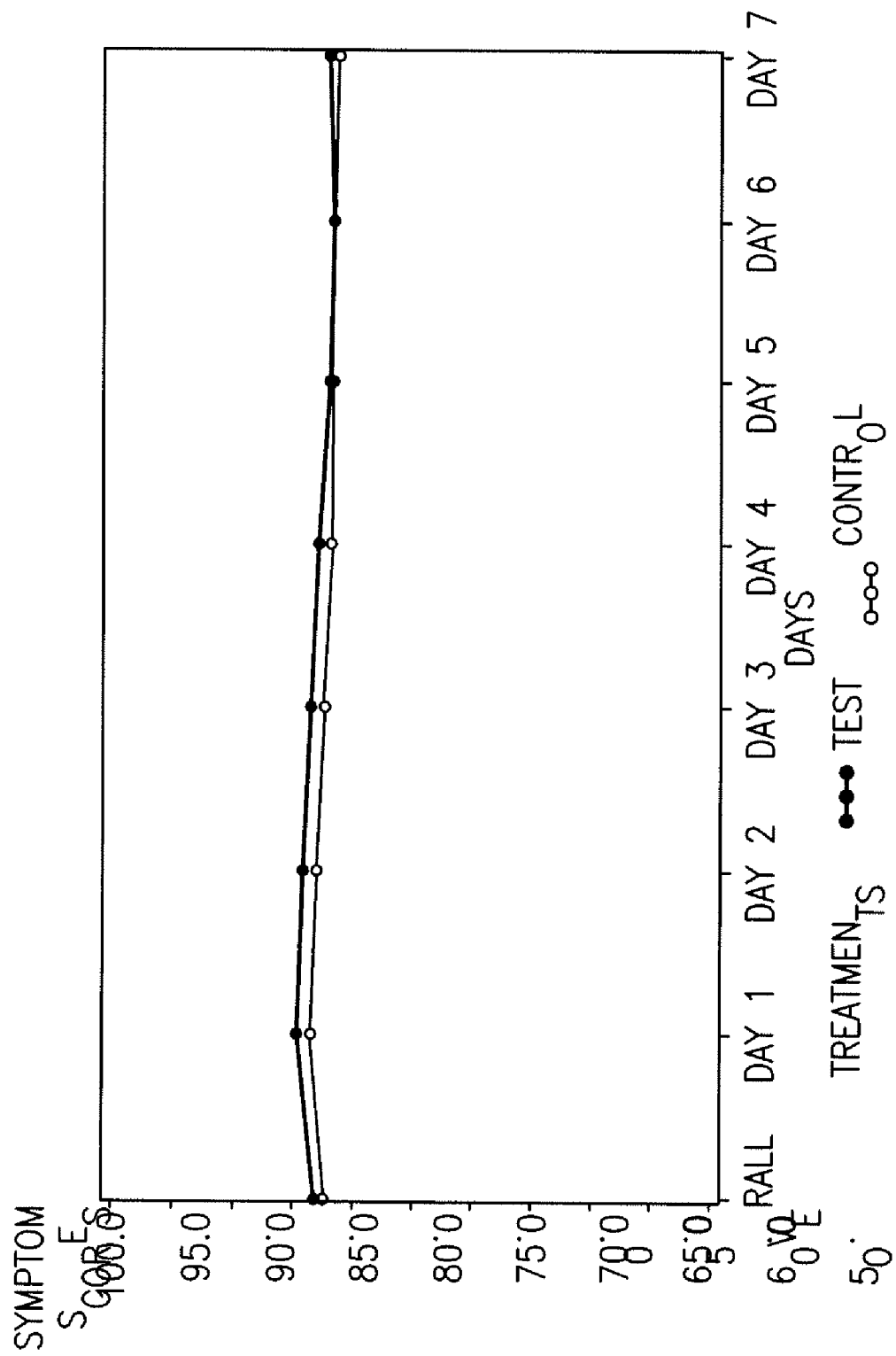
FIG. 4 is a plot showing the overall results of a clinical comparison between the test solution and control solution for cleanliness of lens at end of day.
Figure 5:
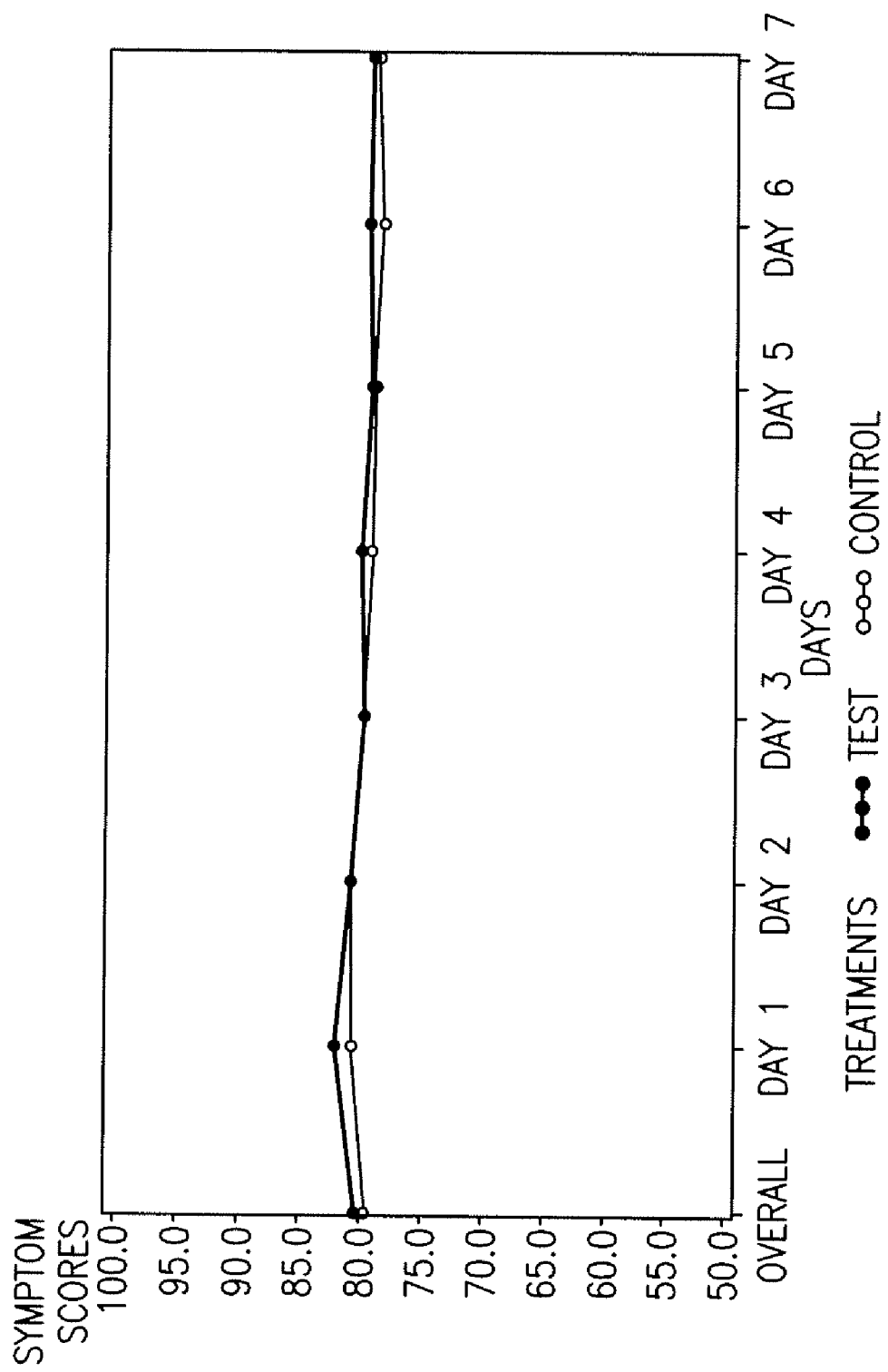
FIG. 5 is a plot showing the overall results of a clinical comparison between the test solution and control solution for comfort at end of day.

Subjects rated their subjective symptoms/complaints using a 0 to 100 scale for each eye. Zero represented the least favorable rating for several lens care characteristics (e.g., end of day comfort, burning/stinging upon insertion of lenses, irritation and dryness) and a 100 represented the most favorable rating. At the two-week follow-up visit, the test solution of Ex. 5 was not statistically significantly different from the control solution for any symptom/complaint. The test solution demonstrated that it was at least as good as the control solution during the first seven days of product use for all diary-lens performance ratings. The overall results for all subjects irrespective of lens type are represented by line plots. FIG. 1 shows the results of a clinical comparison between the test solution and control solution for hours of comfortable wear. FIG. 2 shows the results between the test solution and control solution for cleanliness of lens at insertion. FIG. 3 shows the results between the test solution and control solution for comfort upon insertion. FIG. 4 shows the results between the test solution and control solution for cleanliness of lens at end of day. FIG. 5 shows the results between the test solution and control solution for comfort at end of day.

Dry Eye Results

Sixteen (16) subjects were identified with having dry eye related symptoms for each of the test solution and control solution. Dry eye is defined as an eye at the baseline visit who responded that their eye "often" or "constantly" felt dry and irritated or was ever diagnosed by a physician as having dry eye syndrome. The preliminary results listed in Table 15 suggest that the test solution outperformed the control solution in subjects with dry eye symptoms. For each diary question, scores are compared between the test solution and the control solution using a longitudinal analysis. A score of zero represents a most unfavorable rating and a score of 100 represents a most favorable rating.

TABLE 15

| Performance Criteria | mean (sd) | mean (sd) |
|---|---|---|
| comfort upon insertion | | |
| day 1 | 85 (33) | 75 (33) |
| day 7 | 88 (31) | 71 (33) |
| cleanliness (end of day) | | |
| day 1 | 77 (37) | 61 (37) |
| day 7 | 76 (35) | 61 (37) |
| comfort (end of day) | | |
| day 1 | 73 (35) | 58 (35) |
| day 7 | 74 (33) | 59 (35) |

We claim:

1. An aqueous contact lens cleaning and disinfecting solution composition comprising:
   0.8 ppm to 1.6 ppm of poly(hexamethylene biguanide);
   0.5 ppm to 2 ppm α-[4-tris(2-hydroxyethyl)-ammonium chloride-2-butenyl]poly[1-dimethyl ammonium chloride-2-butenyl]-ω-tris(2-hydroxyethyl)ammonium chloride;
   0.005 wt. % to 0.015 wt. % hyaluronic acid;
   0.01 wt. % to 0.6 wt. % of a sulfobetaine of general formula I

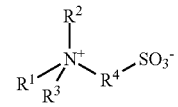

wherein $R^1$ is a $C_8$-$C_{16}$ alkyl optionally substituted with at least one hydroxyl; $R^2$ and $R^3$ are each methyl; and $R^4$ is a $C_2$-$C_4$ alkylene optionally substituted with one hydroxyl;
   a boric acid/borate buffer;
   a nonionic surfactant selected from poloxamer, poloxamine or any combination thereof; and
   sodium chloride, potassium chloride or any combination thereof.

2. The ophthalmic composition of claim 1 wherein the nonionic surfactant is poloxamine with an HLB value from 13 to 28.

3. The ophthalmic composition of claim 1 wherein $R^1$ is a straight, saturated $C_{10}$ alkyl.

4. A method of cleaning and disinfecting a contact lens, the method comprising soaking the contact lens in the ophthalmic composition of claim 1 for at least two hours.

5. The method of claim 4 further comprising inserting the cleaned and disinfected contact lens into the eye without rinsing the lens after soaking.

6. The composition of claim 1 further comprising dexpanthenol, sorbitol, glycolic acid, 2-amino-2-methyl-1,3-propanediol or any mixture thereof.

7. The composition of claim 1 further comprising citrate, citric acid or a mixture thereof.

8. The composition of claim 1 further comprising propylene glycol, hydroxypropyl guar or myristamidopropyl dimethylamine.

9. The composition of claim 1 further comprising hydroxypropylmethyl cellulose.

10. An aqueous contact lens care solution composition comprising:
    1 ppm to 1.3 ppm of poly(hexamethylene biguanide);
    1 ppm α-[4-tris(2-hydroxyethyl)-ammonium chloride-2-butenyl]poly[1-dimethyl ammonium chloride-2-butenyl]-ω-tris(2-hydroxyethyl)ammonium chloride;
    0.008 wt. % to 0.015 wt. % hyaluronic acid; and
    a borate buffer system component selected from the group consisting of boric acid and borate.

11. The solution of claim 10 further comprising a nonionic surfactant selected from poloxamer, poloxamine or any combination thereof; and
    sodium chloride, potassium chloride or any combination thereof.

12. A method of cleaning and disinfecting a contact lens, the method comprising soaking the contact lens in the ophthalmic composition of claim 10 for at least two hours.

* * * * *